US00PP08687P

United States Patent [19]

de Jong

[11] Patent Number: Plant 8,687

[45] Date of Patent: Apr. 12, 1994

[54] KATJANA

[75] Inventor: Cornelis T. J. de Jong, CR Roelofarendsveen, Netherlands

[73] Assignee: Agroplant-Select BV, De Kwakel, Netherlands

[21] Appl. No.: 36,652

[22] Filed: Mar. 24, 1993

[51] Int. Cl.[5] ..... A01H 5/00

[52] U.S. Cl. ..... Plt./87.1

[58] Field of Search ..... Plt. 87.1

*Primary Examiner*—James R. Feyrer

[57] ABSTRACT

A new and distinct cultivar of Alstroemeria plant named Katjana, characterized by its reddish-purple outer petals and the bright yellow and cream coloring of the inner two-thirds of the top inner petals length and strong dark streaking on the inside portion of the entire inner petal body.

1 Drawing Sheet

BACKGROUND OF THE INVENTION

The present invention comprises a new and distinct cultivar of Alstroemeria plant referred to by the cultivar name Katjana. Katjana was originated from a hybridization program in Roelofarendsveen, The Netherlands in 1985. Each of the parent plants were proprietary hybrids, and have not been released or marketed, and are maintained strictly for use in the breeding program. Katjana was discovered and selected as one flowering plant within the progeny of the stated parentage by me on Jul. 21, 1985 in a controlled environment in Roelofarendsveen, The Netherlands. The first asexual reproduction of Katjana was accomplished when vegative cuttings were taken from initial selection on Nov. 6, 1985 in a controlled environment in Roelofarendsveen in The Netherlands. Horticultural examination of selected units initiated in November 1985 has demonstrated that the combination of characteristics as herein disclosed for Katjana are firmly fixed and retained through generations of asexual reproduction. The following observations, measurements and comparisons describe plants grown in Roelofarendsveen, The Netherlands under greenhouse conditions which apporixmate those generally used in commercial practice. The following traits have been repeatedly observed and are determined to be basic characteristics of Katjana, which in combination distinguish this Alstroemeria from its parent and all other varieties of which I am aware:

1. The outer petals have a distinctive reddish-purple color, which is strongest in a blush in the central area below the green tip. These three petals contain a faint pattern of subdued dark reddish-purple stripes in irregular patterns substantially confined to the marginal portions of the lobes of these petals.
2. The inner petals are characterized by an unusual combination of colors and pattern of stripes. The tops and bottoms of the two top inner petals are shaded with light red-purple coloration which is most intensive at the apex. A broad band of creamy-white occupies about half of the area of each top inner petal, and dominates the central portion of each of these petals; suffusing gradually to the red-purple at the tops and bottoms. The central portion of the white band is strongly shaded with a bright yellow spot which is strongest in the middle of each of these petals and blends progressively to the creamy-white color of the band from the center of the petal. These two petals conain a myriad of conspicuous dark reddish-purple stripes which are short and narrow at the base of the petal and increase in length and width with increasing distance from the attachment points of petals. The bottom inner petal contains similar reddish-purple color, and stripes but does not contain a central creamy-white band and the stripes are substantially confined to the apical half of this petal.
3. The startling combination of petal colors and markings of the flowers of this plant give dramatic and attractive distinction to this variety which has not been seen in previous plants of this market class.

BRIEF DESCRIPTION OF THE FIGURE OF THE DRAWING

The accompanying photographic drawing of a close-up of the flower in bloom and buds shows typical inflorescence and foliage characteristics of Katjana nearly as true as possible with illustrations of this type. In the following description, color references are made to The Royal Horticultural Society Color Chart (RHS). The color values were determined in the afternoon in May 1988 at Roelofarendsveen, The Netherlands.

BOTANICAL DESCRIPTION OF THE PLANT

Botanical: Alstroemeria cv Katjana.
Commercial: Alstroemeria.

PLANT

A. General appearance:

*Form.*—Typical of genus, of about lower than average height for the market class; upright stems, spreading by rhizomes, bush forming.

*Height.*—Measured from the surface of the soil to the highest flowers: Summer: about 120–150 cm. Winter: about 150–200 cm. (If grown as a bedding plant outside, the height will be about 40 cm during the summer and about 50 cm during the winter).

*Growth.*—Upright, spreading through rhizomes, vigor is average. Use of this plant is for cut flower production.

B. Foliage:

*Quantity.*—Medium.

*Stems.*—When mature: about 50–70 per plant, per year.

*Number of leaves.*—Varying from season to season through the year: Summer: about 20 per stem. Winter: about 30 per stem.

*Internode.*—Length: about 10 cm, varies with light intensity and season.

*Size of leaf.*—Length: Long, about 11 cm. Width: Broad, about 3.5 cm

*Shape of leaf.*—Elliptical.

*Color of leaf.*—Typical of the genus. upper side: dark green. under side: dark green.

*Texture.*—Smooth.

C. Rhizomes:

*Color.*—White.

*Size.*—Average.

INFLORESCENCE

A. Bud:

*Form.*—Normal elliptical.

*Size.*—Diameter: About 2.5 cm just prior to opening. Length: About 3 cm.

*Receptacle.*—Broadly elliptical.

B. Flower:

*Flower production.*—High: about 50–70.

*Size.*—Width: about 6 cm. Depth: about 4 cm.

*Borne.*—Umbel of about 5 branches of substantially uniform length; each bearing about 5 or more buds on short peduncles.

*Blooming habit.*—When grown under controlled conditions: continuous the year around. The plant would bloom freely when grown as a bedding plant. Blind stems are produced in the fall and winter.

*Outer petals.*—Shape: lobed. Size: Length: about 3 cm. Width: about 2 cm. Color: Reddish-purple color near to RHS 60-D which is strongest in a blush, in the central area below the green tip; and, dark reddish purple stripes in irregular patterns substantially confined to the marginal portions of the lobes. Reverse side: near to 60-D. Margins: very finely dentate.

*Inner petals.*—Shape: lanceolate. Size: Length: About 2.5 cm. Width: About 1–1.5 cm. Color: Upper petals: From adjacent base towards the upper most portion cream with yellow colored near to RHS 4-A. Upper most portion of the body near to 60-D, with a myriad of conspicuous dark reddish-purple stripes which are short and narrow at the base of the petal and increase in length and width with increasing distance from the attachment points of the petals. Reverse side: Near to 60-D with some creme-yellow. Bottom petal: Similar reddish-purple color — 60-D — as the outer petals with long dark purple stripes which are substantially confined in the apical half, with some smaller purple stripes near the margins. Reverse side: Near to 60-D. Margins: Irregular undulations.

*Peduncle.*—Color: Medium green. Length: About 12.5 cm.

*Fragrance.*—None.

*Lasting quality.*—Approximately 14 days.

C. Reproductive organs:

*Size.*—Typical for genus.

*Stamens.*—Number: 6.

*Anthers.*—Color: green-yellow.

*Filaments.*—Color: Light purple.

*Pistils.*—Color: Strong anthocyanin. Number: 1.

*Stigma.*—Color: Anthocyanin.

*Fertility.*—Very easy.

I claim:

1. A new and distinct cultivar of Alstroemeria named Katjana, as illustrated and described herein, characterized by its reddish-purple outer petals and the bright yellow and cream coloring of the inner two-thirds of the top inner petals length and strong dark streaking on the inside portion of the entire inner petal body.

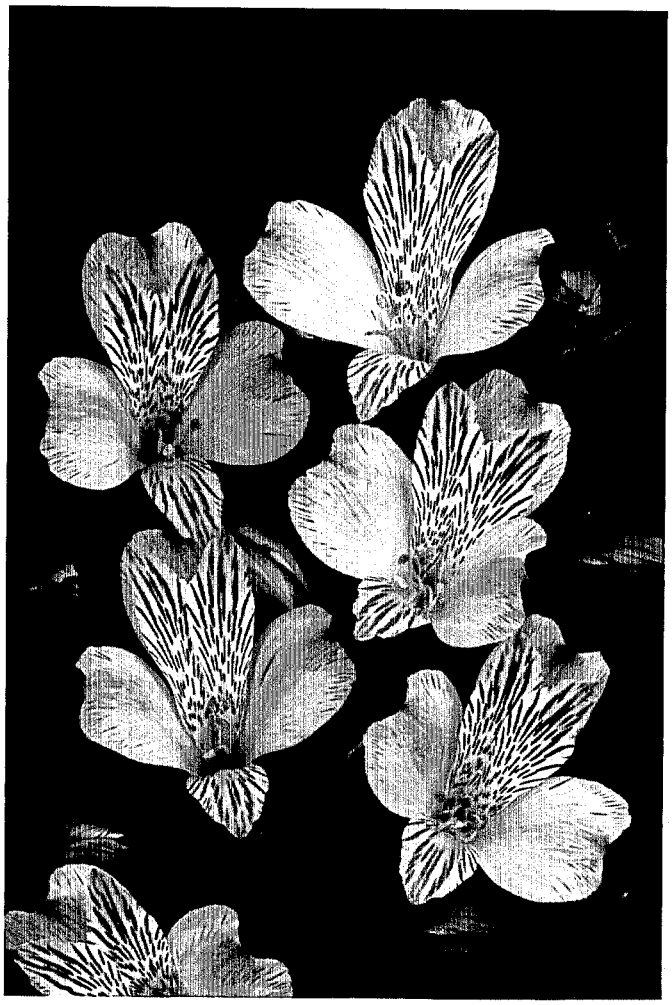

* * * * *